US00PP24225P3

(12) United States Plant Patent
Olesen

(10) Patent No.: US PP24,225 P3
(45) Date of Patent: Feb. 11, 2014

(54) *ROSA* HYBRID VARIETY DENOMINATION 'POULCAS034'

(50) Latin Name: ***Rosa* hybrid**
Varietal Denomination: Poulcas034

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 58 days.

(21) Appl. No.: 13/507,023

(22) Filed: May 31, 2012

(65) Prior Publication Data

US 2013/0326767 P1 Dec. 5, 2013

(51) Int. Cl.
*A01H 5/00* (2006.01)

(52) U.S. Cl.
USPC ..... Plt./151

(58) Field of Classification Search
USPC ..... Plt./151, 150
See application file for complete search history.

*Primary Examiner* — Annette Para

(57) ABSTRACT

A new garden rose plant of the Floribunda class which has abundant, red flowers and attractive foliage. This new and distinct variety has shown to be uniform and stable in the resulting generations from asexual propagation.

1 Drawing Sheet

Botanical designation: *Rosa* hybrid.
Variety denomination: 'Poulcas034'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2002 and the resulting seeds were planted in a controlled environment in Fredensborg, Denmark. The new variety, named 'Poulcas034', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas034' from all other varieties of which we are aware.

As part of the rose development program, Mogens N. Olesen germinated the seeds from the aforementioned hybridization during winter of 2002 and conducted evaluations on the resulting seedlings in a controlled environment in Fredensborg, Denmark. 'Poulcas034' was selected in the spring of 2003 by the inventor as a single plant from the progeny of the aforementioned hybridization.

Asexual reproduction of 'Poulcas034' by traditional budding and rooted cuttings was first done by Mogens N. Olesen in the nursery in Fredensborg, Denmark in July, 2003. This initial and other subsequent asexual propagations conducted in controlled environments have demonstrated that the characteristics of 'Poulcas034' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulcas034'. Specifically illustrated in the drawing are flowers at various stages of development, flower in parts, leaves, and stems.

DETAILED DESCRIPTION OF THE VARIETY

The following is a description of 'Poulcas034', as observed in its growth in in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulduf', U.S. Plant patent application Ser. No. 11/331,698, now abandoned, are compared to 'Poulcas034' in Chart 1.

CHART 1

| | 'Poulcas034' | 'Poulduf' |
|---|---|---|
| Petal Count | 70, 5 to 7 of which are petaloids. | 35 to 40. |
| Flower Diameter | 90 to 100 mm. | 110 to 120 mm. |
| General Tonality of Flower Color | Red Group 45B. | Red Group 53C. |

FLOWER AND FLOWER BUD

Blooming habit: Continuous.
Flower bud:

*Size*.—Upon opening, 22 mm in length from base of receptacle to end of bud. Bud diameter is 18 mm.

*Bud form*.—Ovoid.

*Bud color*.—As sepals divide the petal color is Red-Purple Group 59A.

*Sepal inner surface*.—Color: Green Group 138B with weak intonations of Greyed-Orange Group N167A. Surface: Smooth and pubescent.

*Sepal outer surface*.—Color: Yellow-Green Group 144A with moderate intonations of Greyed-Red Group 178B. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—27 mm long by 8 mm wide.

*Receptacle*.—Texture: Smooth. Size: 6 mm in height by 5 mm wide. Color: Yellow-Green Group 144A with intonations of Greyed-Red Group 178B. Shape: Campanulate.

*Pedicel*.—Surface: Rough, with moderate amount of small prickles. Length: 40 to 50 mm. Diameter: 3 mm on average. Color: Yellow-Green Group 144A with anthocyanic pigments the color of Greyed-Red Group 178A. Strength: Strong.

*Peduncle*.—Length: Varying from 4 to 13 cm. Diameter: 3 to 4 mm. Color: Yellow-Green Group 144A with anthocyanic pigments the color of Greyed-Red Group 178A.

Flower bud development: Flower buds are borne both singly, and in clusters of 3 to 5 flower buds per stem, resembling a corymb.

Flower bloom:

*Fragrance*.—Light flora.

*Duration*.—The blooms have a duration on the plant of approximately 10 to 15 days. Petals persist on the receptacle after flowers have fully matured.

*Size*.—Flower diameter is 90 to 100 mm when open. Flower depth is 38 mm.

*Flower shape*.—General shape is a quartered-rosette, very double, with many overlapping petals packed into quarter sections.

*Shape of flower, side view*.—Upon opening the upper portion is flat. The lower portion is a flattened convex.

Petalage: Under normal conditions, flowers have 70 petals total, 5 to 7 of which are petaloids.

General tonality of flower: Open flowers are Red Group 45B. Tonality does not change.

Petal color: The petal color remains the same for outer and inner petals, upon opening and after opening.

*Upper surface*.—Red Group 45B with Yellow Group 8D at the petal base.

*Lower surface*.—Red Group 53C with Yellow Group 8D at the petal base.

Petals:

*Petal reflex*.—Very weak.

*Margin*.—Entire and uniform. Weak undulations observed.

*Shape*.—Generally narrow elliptic. Apex shape: Rounded. Base shape: Acute.

*Size*.—45 mm (l)×40 mm (w).

*Texture*.—Smooth.

*Thickness*.—Average.

Petaloids:

*Size*.—16 mm (l) by 6 mm (w).

*Quantity*.—5 to 7.

*Shape*.—Asymmetric, with a rounded apex and acute base.

*Color*.—Same as petal color.

Reproductive organs:

*Pollen*.—None observed.

*Anthers*.—Size: 2 mm in length. Color: Yellow-Orange Group 18A. Quantity: 50 on average.

*Filaments*.—Color: Orange-Red Group N134C. Length: 6 mm.

*Pistils*.—Length: 6 to 7 mm. Quantity: 45 on average.

*Stigmas*.—Color: Yellow-White Group 158A.

*Styles*.—Color: Yellow-White Group 158A.

*Location of stigmas*.—Superior in location relative to the length of the filaments and the height of the anthers.

*Hips*.—None Observed.

PLANT

Plant growth: Upright, bushy. Plants are 40 cm in height, and 40 cm wide.

Stems:

*Color*.—Juvenile growth: Yellow-Green Group 144A with Greyed-Purple Group 183C. Mature growth: Yellow-Green Group 144A.

*Length*.—On average, canes are 25 cm from the base of the plant to the flowering portion.

*Diameter*.—5 mm.

*Internodes*.—On mature canes, there is an average distance of 30 mm between nodes.

*Surface texture*.—Young wood: Smooth. Older wood: Smooth.

Long prickles:

*Incidence*.—10 prickles per 10 cm of stem.

*Size*.—Average length of prickles on mature stems is 6 mm.

*Shape*.—Upper portion is linear. Lower portion is concave.

*Color*.—Juvenile prickles: Greyed-Purple Group 185A. Mature prickles: Greyed-Orange Group 164B.

Plant foliage:

*Compound leaf*.—100 mm (l)×80 (w).

*Quantity*.—3 leaves per 10 cm of stem on average.

*Leaf bearing angle to the stem*.—45 degrees.

*Color of juvenile foliage*.—Upper side: Yellow-Green Group 146A. Lower side: Yellow-Green Group 146B. Anthocyanin: Generalized throughout the leaflet, and covering the margins, Greyed-Purple Group 184A.

*Color of mature foliage*.—Upper side: Yellow-Green Group 147A. Lower side: Yellow-Green Group 147B.

Plant leaves and leaflets:

*Stipules*.—Size: 20 mm in length. Quantity: 2 per compound leaf. Shape: Linear, slightly broad based with outward extending apecies. Margins: Finely serrated. Color: Yellow-Green Group 146B.

*Petiole*.—Length: 20 mm. Diameter: 2 mm.

*Upper surface*.—Color: Yellow-Green Group 144A with Greyed-Purple Group 184A.

*Lower surface*.—Color: Yellow-Green Group 144B. Observations: Smooth.

*Rachis*.—Length: 40 mm.

*Upper surface*.—Color: Yellow-Green Group 144A with Greyed-Purple Group 184A.

*Lower surface*.—Color: Yellow-Green Group 144B. Observations: Smooth.

*Leaflet*.—Quantity: Normal number of leaflets leaves in middle of the stem is 5 leaflets. Margins: Serrated. Size: Average size of the terminal leaflet on normal leaves is 52 mm in length by 41 mm wide. Shape: Generally ovate. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery and downy mildew, rust, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

It is claimed:

1. A new and distinct variety of rose plant of the Floribunda rose class named 'Poulcas034', substantially as illustrated and described herein, due to its abundant red flowers, disease resistance, and extended period of bloom.

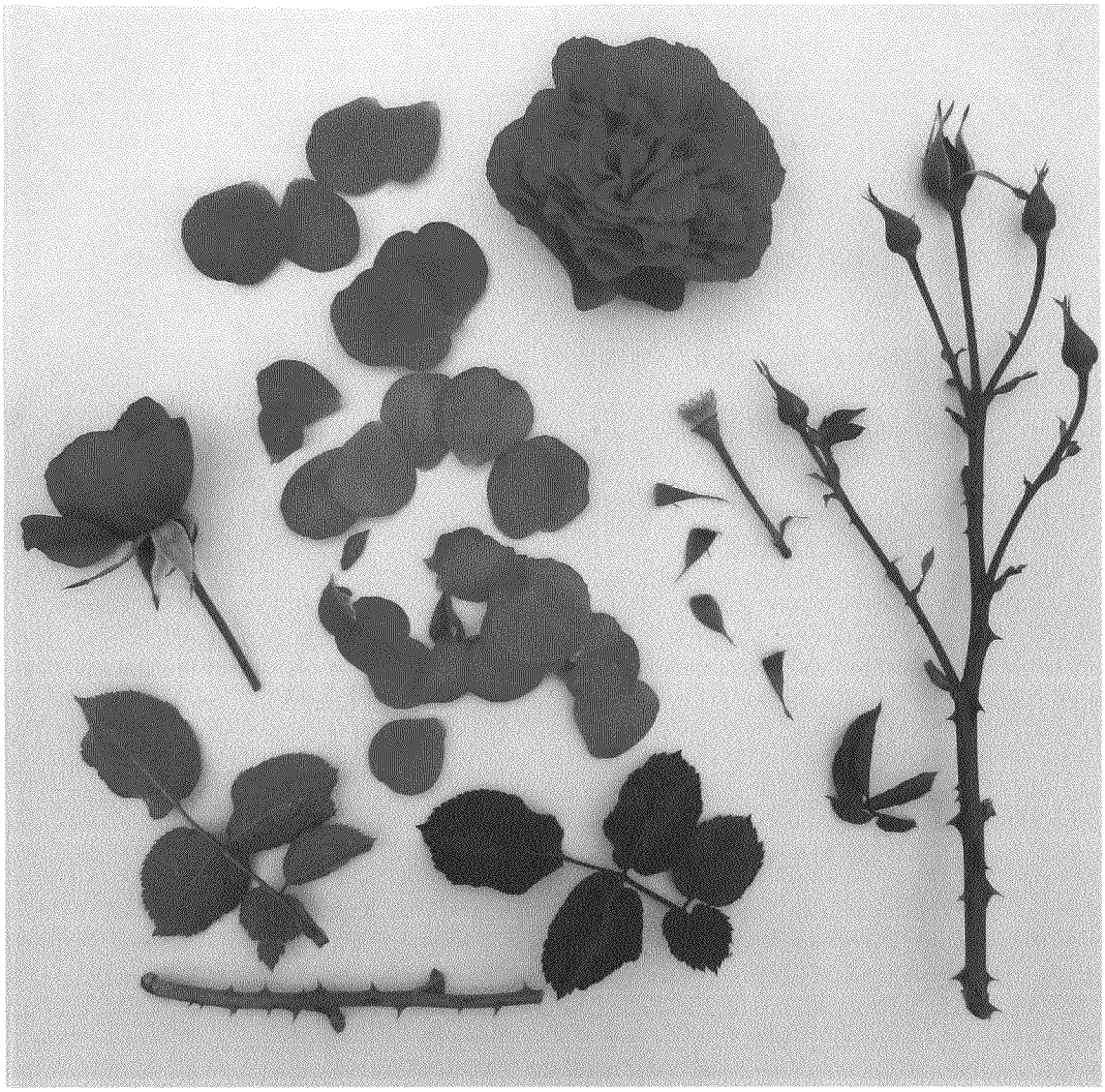

* * * * *